United States Patent
Pitaoulis

(10) Patent No.: US 11,672,624 B2
(45) Date of Patent: Jun. 13, 2023

(54) DISPOSABLE DUAL ACCESS CATHETERIZATION SLEEVE

(71) Applicant: TESSLAGRA DESIGN SOLUTIONS INC, Staten Island, NY (US)

(72) Inventor: Christos Pitaoulis, Brooklyn, NY (US)

(73) Assignee: TESSLAGRA DESIGN SOLUTIONS, INC, Staten Island, NY (US)

(*) Notice: Subject to any disclaimer, the term of this patent is extended or adjusted under 35 U.S.C. 154(b) by 200 days.

(21) Appl. No.: 17/037,640

(22) Filed: Sep. 29, 2020

(65) Prior Publication Data
US 2021/0007821 A1  Jan. 14, 2021

Related U.S. Application Data

(63) Continuation-in-part of application No. 13/273,796, filed on Oct. 14, 2011, now Pat. No. 11,304,773.

(60) Provisional application No. 61/394,815, filed on Oct. 20, 2010.

(51) Int. Cl.
*A61B 46/27* (2016.01)
*A61B 46/20* (2016.01)

(52) U.S. Cl.
CPC ........ *A61B 46/27* (2016.02); *A61B 2046/205* (2016.02)

(58) Field of Classification Search
CPC .... A61B 46/00–40; A61M 2025/0266; A61M 2025/0273; A61M 25/01; A61M 2025/0246; A61F 13/00–0293; A61F 13/06–069
See application file for complete search history.

(56) References Cited

U.S. PATENT DOCUMENTS

| | | | |
|---|---|---|---|
| 3,424,153 A | | 1/1969 | Lewis, Jr. |
| 3,667,458 A | * | 6/1972 | Krebs ............ A61L 15/58 |
| | | | 128/853 |
| 3,707,964 A | | 1/1973 | Patience et al. |
| 3,769,971 A | | 11/1973 | Collins |
| 3,989,040 A | * | 11/1976 | Lofgren ............ A61B 46/27 |
| | | | 128/856 |
| 4,470,410 A | | 9/1984 | Elott |
| 4,582,508 A | | 4/1986 | Favelka |
| 4,633,863 A | | 1/1987 | Filips et al. |
| 4,745,915 A | | 5/1988 | Enright et al. |
| 4,911,151 A | | 3/1990 | Rankin et al. |
| 5,010,617 A | | 4/1991 | Nelson |
| 5,178,162 A | | 1/1993 | Bose |

(Continued)

OTHER PUBLICATIONS

Notice of Allowance for U.S. Appl. No. 13/273,796 dated Dec. 30, 2021.

*Primary Examiner* — Michelle J Lee
(74) *Attorney, Agent, or Firm* — F. Chau & Associates, LLC

(57) ABSTRACT

A dual access catheterization sleeve includes a first panel and a second panel attached to each other along sides thereof and at one end, wherein a closed distal end and an open proximal end are formed, a first access fenestration formed through the first panel at a location in a center portion of the sleeve between the proximal and distal ends; and a second access fenestration formed through the first panel at a location between the first access fenestration and the closed distal end. The sleeve is dimensioned to cover a hand and at least a portion of an arm of a patient.

4 Claims, 6 Drawing Sheets

(56) References Cited

U.S. PATENT DOCUMENTS

| | | | |
|---|---|---|---|
| 5,238,010 A | 8/1993 | Grabenkort et al. | |
| 5,342,286 A | 8/1994 | Kelly et al. | |
| 5,415,642 A | 5/1995 | Shepherd | |
| 5,437,621 A | 8/1995 | Andrews et al. | |
| 5,562,107 A | 10/1996 | Lavender et al. | |
| 5,785,057 A | 7/1998 | Fischer | |
| 5,807,341 A | 9/1998 | Heim | |
| 5,975,082 A * | 11/1999 | Dowdy | A61B 46/00 128/853 |
| 5,978,082 A | 11/1999 | Terui et al. | |
| 6,014,774 A | 1/2000 | Davey et al. | |
| 6,298,855 B1 * | 10/2001 | Baird | A61B 46/00 128/853 |
| 6,571,395 B1 | 6/2003 | Korkor | |
| 6,694,981 B2 * | 2/2004 | Gingles | A61B 46/00 128/853 |
| 7,063,447 B2 | 6/2006 | Hill et al. | |
| 7,678,092 B2 | 3/2010 | Matloub et al. | |
| 8,206,363 B2 * | 6/2012 | Bainbridge | A61B 46/27 604/293 |
| 2003/0150044 A1 | 8/2003 | Hoy | |
| 2007/0073227 A1 | 3/2007 | Hewes et al. | |
| 2009/0247966 A1 | 10/2009 | Williams | |
| 2012/0097176 A1 | 4/2012 | Pitaoulis | |
| 2013/0125901 A1 | 5/2013 | Pitaoulis | |

\* cited by examiner

DISPOSABLE DUAL ACCESS CATHETERIZATION SLEEVE

CROSS-REFERENCE TO RELATED APPLICATIONS

This application is a continuation-in-part of U.S. application Ser. No. 13/273,796, filed on Oct. 14, 2011 in the U.S. Patent and Trademark Office, which in turn claims priority from U.S. Provisional Appl. No. 61/394,815, filed on Oct. 20, 2010 in the U.S. Patent and Trademark Office, the contents of both of which are herein incorporated by reference in their entireties.

BACKGROUND

1. Technical Field

The invention relates to a disposable sleeve that can be used to provide sterility during a surgical procedure in which a blood vessel in a patient's arm or wrist is accessed.

2. Discussion of the Related Art

Cardiac catheterization is a medical procedure that inserts a catheter into a blood vessel at a location spaced from the heart. The catheter then is advanced through the blood vessel to a location near the heart and is used to guide surgical tools or prosthetic components into the region of the heart. For example, cardiac catheterization may be used to repair a damaged section of the blood vessel or a damaged valve or to implant a graft or stent.

For many years, cardiac catheterization was carried out by accessing the femoral artery in a portion of the thigh near the groin. More recently, cardiac catheterization has been carried out by accessing a blood vessel in the wrist or forearm. Cardiac catheterization that accesses a blood vessel in the wrist area generally is referred to as radial access catheterization. Catheterization that accesses a blood vessel closer to the elbow area of the forearm generally is referred to as brachial catheterization.

A patient typically is lying prone on an operating table during a radial or brachial access catheterization procedure. The arm that will be accessed is supported on a lateral extension of the operating table. Thus, doctors and other medical personnel who will be involved in the procedure will be on the side of the patient with the arm that will be accessed and in proximity to the arm during the procedure.

Sterility is extremely important during all invasive medical procedures. Medical personnel performing the procedure take steps to scrub and/or cover parts of their body. Areas of the patient near the access or entity site must be sterilized and must be isolated from parts of the patient that are not sterilized. Areas near the entry site are likely to be shaved, scrubbed and wiped with an antiseptic solution. Sterile sheets or drapes then are placed over other areas of the patient and are taped or otherwise secured to the patient to ensure that non-sterile areas of the patient do not adversely affect areas near the entry side that have been cleaned.

Cardiac catheterization that accesses the femoral artery will sterilize areas near the access site in the upper thigh or groin area. Sterile surgical drapes then will be positioned on the operating table and over the patient to cover the torso, the leg that is not being accessed and the lower part of the leg that is being accessed. These drapes are secured to the patient and areas of these sterile surgical drapes that extend beyond the patient can be positioned conveniently on the operating table in a manner that will not interfere with the doctor and other medical personnel.

Cardiac catheterization that enters the blood vessel in the patient's forearm typically has utilized the same sterile surgical drapes that are used for cardiac catheterization that accesses the thigh. However, the size and orientation of the extension of the operating table on which the arm is supported and the size and shape of the arm complicates efforts to use traditional sterile surgical drapes. More particularly, the drapes are likely to hang over the sides of the operating table extension on which the arm is supported and are prone to being displaced. Doctors are likely to improvise arrangements of clamps, tapes and the like in efforts to hold the sterile surgical drapes in a position that permit access to the location on the patient where the blood vessel will be entered while also keeping other non-sterile areas of the patient covered and isolated from the site of the surgical entry. A patient who is undergoing cardiac catheterization also typically has a blood oxygen monitor clipped to a finger. The presence of a blood oxygen monitor on a finger of the arm that is being accessed further complicates efforts to maintain sterility at the surgical access site.

SUMMARY

According to an embodiment of the disclosure, there is provided a catheterization sleeve that includes a first panel and a second panel attached to each other along sides thereof and at one end, wherein a closed distal end and an open proximal end are formed; a first sleeve fenestration formed through the first panel at a location in a center portion of the first panel between the proximal and distal ends; a second sleeve fenestration formed through the first panel at a location between the first sleeve fenestration and the closed distal end; a first clear film that covers the first sleeve fenestration and is attached to the first panel at an edge region of the first panel adjacent to the first sleeve fenestration; a second clear film that covers the second sleeve fenestration and is attached to the first panel at an edge region of the first panel adjacent to the first sleeve fenestration; a first foldable flap that covers the first clear film and the first sleeve fenestration; and a second foldable flap that covers the second clear film and the second sleeve fenestration. The first foldable flap includes a first liner removably attached to an inner surface of the first foldable flap that faces the first clear film and the first sleeve fenestration when the first foldable flap is in a closed position, and a first flap fenestration the penetrates the first foldable flap and the first liner, and the first flap fenestration of the first foldable flap is aligned with the first sleeve fenestration when the first foldable flap is in a closed position, and a size of the first flap fenestration is less than or equal to a size of the first sleeve fenestration. The second foldable flap includes a second liner removably attached to an inner surface of the second foldable flap that faces the second clear film and the second sleeve fenestration when the second foldable flap is in a closed position and a second flap fenestration the penetrates the second foldable flap and the second liner, and the second flap fenestration of the second foldable flap is aligned with the second sleeve fenestration when the second foldable flap is in a closed position, and a size of the second flap fenestration is less than or equal to a size of the second sleeve fenestration. The sleeve is dimensioned to cover a hand and at least a portion of an arm of a human patient According to a further embodiment of the disclosure, the catheterization sleeve includes an adhesive substantially adjacent to the open proximal end for securing the proximal end of the sleeve to the patient at a location in proximity to a shoulder of the patient, and a removable cover that covers the adhesive.

According to a further embodiment of the disclosure, the first clear film and the second clear film are each removably attached to the first panel by an adhesive, and wherein each of the first and second clear films includes a pull tab attached thereto, wherein each of the first or second clear films is removed from the first panel by application of a pulling force to the pull tab.

According to a further embodiment of the disclosure, the first foldable flap is securely attached to the first panel wherein the first foldable flap can be folded back to expose the first clear film; and the second foldable flap is securely attached to the first panel wherein the second foldable flap can be folded back to expose the second clear film.

DETAILED DESCRIPTION OF EXEMPLARY EMBODIMENTS

Figure 1:
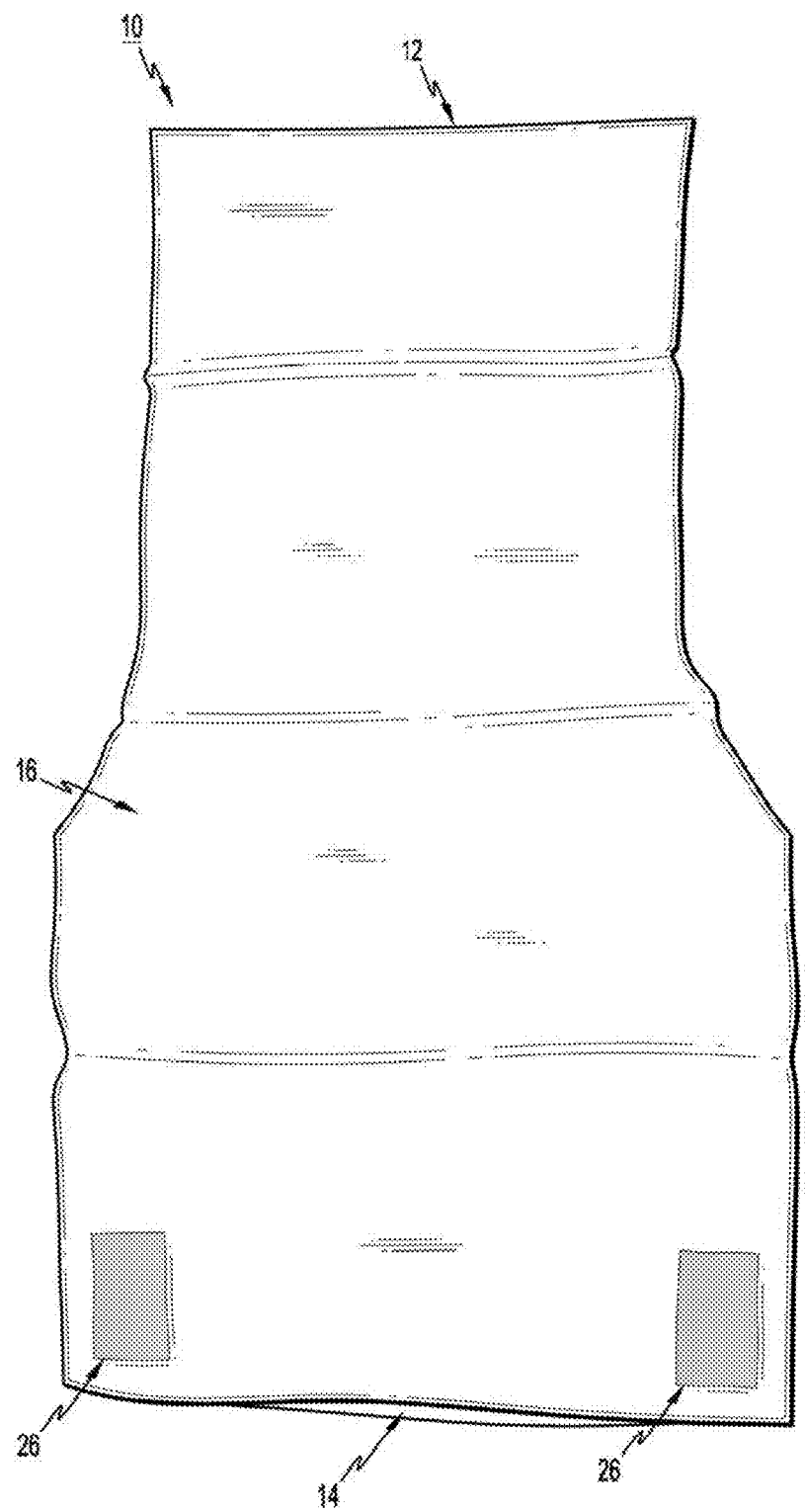
FIG. 1 is a bottom plan view of a sleeve according to an embodiment of the disclosure.

Exemplary embodiments of the disclosure as described herein generally provide a disposable dual access catheterization sleeve. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Figure 2:
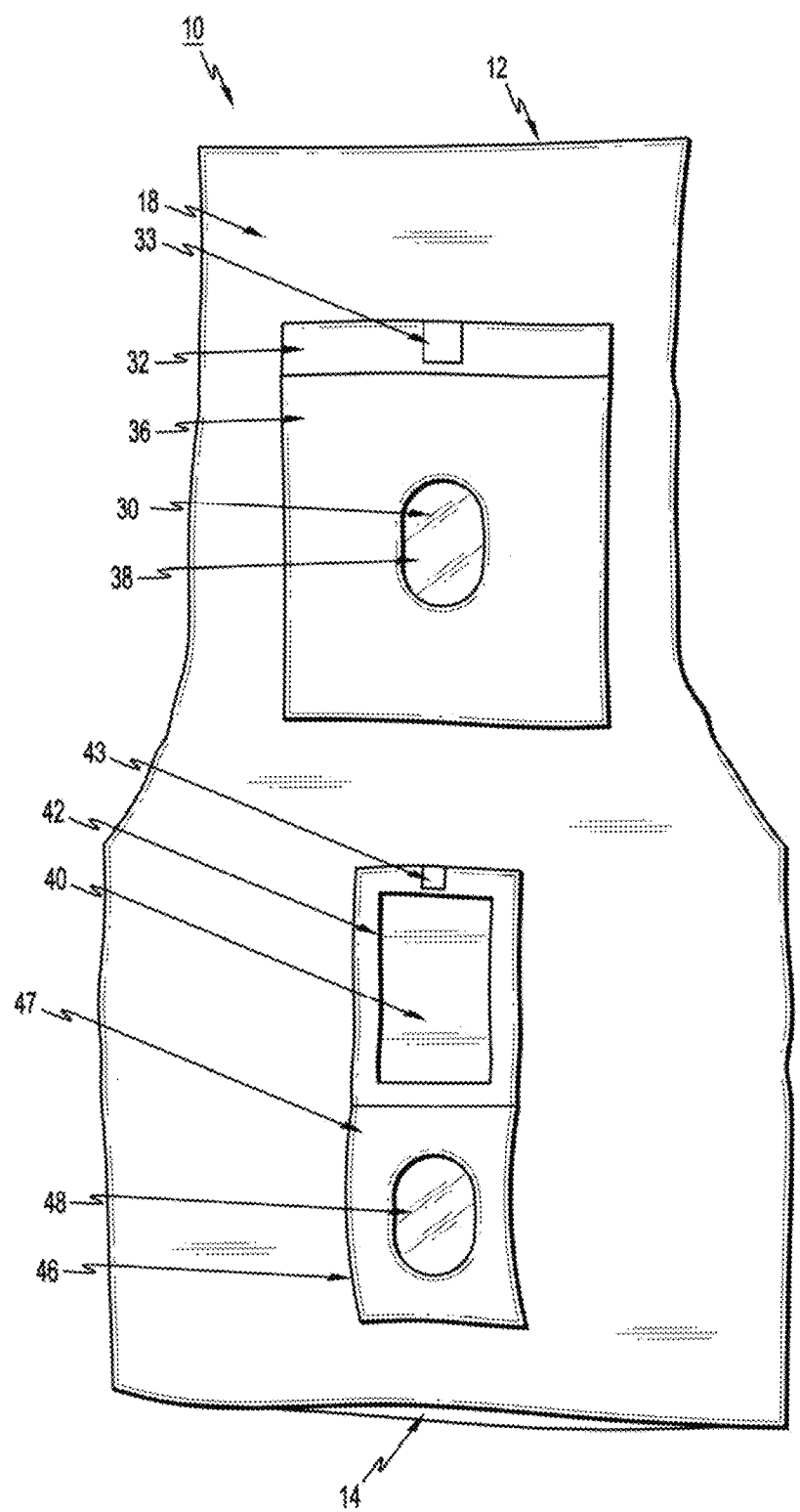
FIG. 2 is a top plan view of a sleeve according to an embodiment of the disclosure.
Figure 3:
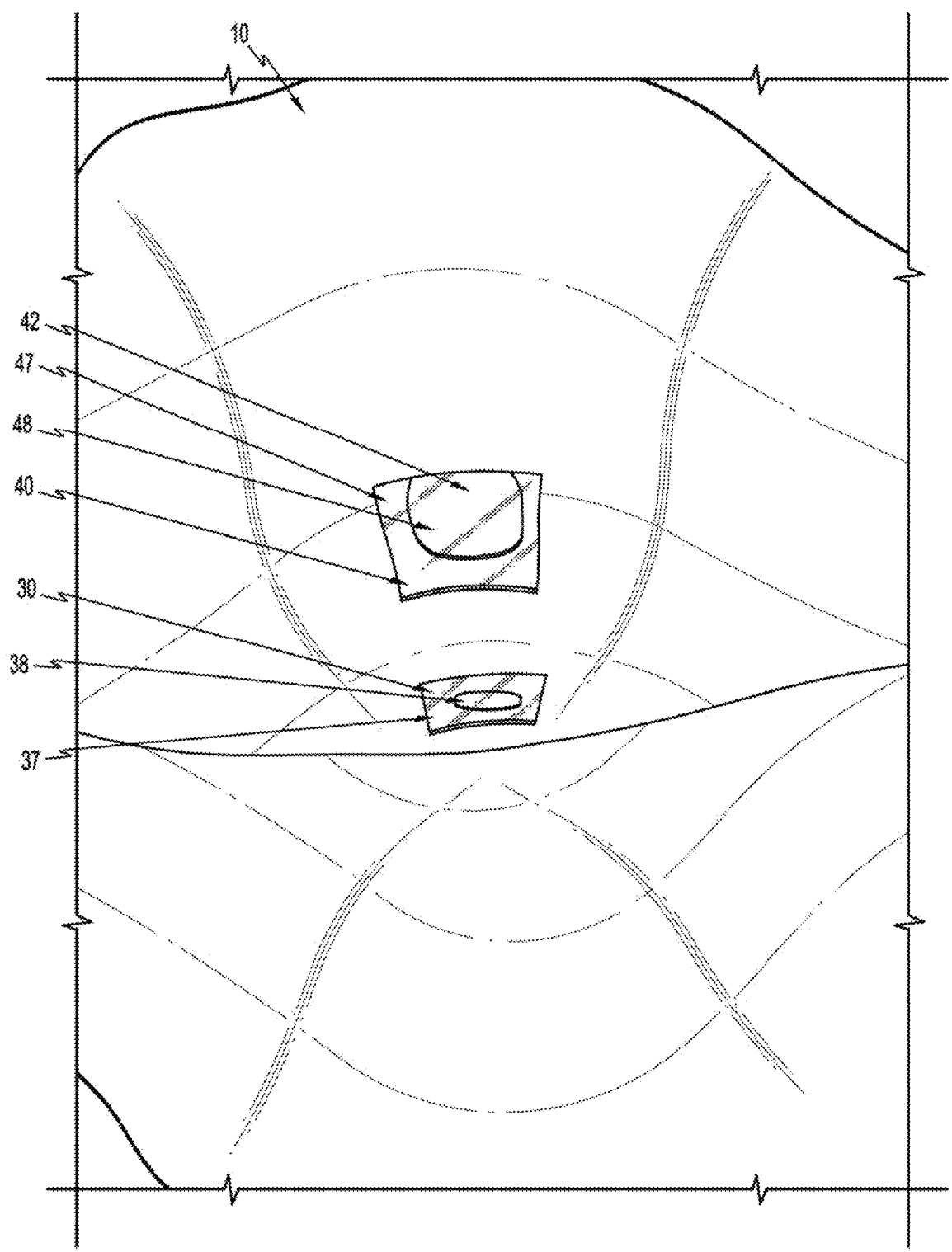
FIG. 3 is a view looking into the sleeve from the open end, according to an embodiment of the disclosure.

A radial or brachial access catheterization sleeve in accordance with an embodiment of the disclosure is identified generally by the numeral 10 in FIGS. 1-7. The sleeve 10 is formed from a flexible plastic, such as polypropylene, or alternatively from a flexible nonwoven fabric or paper material that is coated with plastic or other fluid impermeable material and may be formed from materials currently used for disposable medical or surgical drapes. FIG. 1 is a bottom plan view of a sleeve according to an embodiment of the disclosure, and FIG. 2 is a top plan view of a sleeve according to an embodiment of the disclosure. Referring now to FIGS. 1-2, the sleeve 10 has a closed end 12, an open end 14, and is formed from a first panel 16 and a second panel 18 that are joined together at each side and at the closed end 12. In some embodiments, the first panel 16 and second panel 18 are integrally formed. The sleeve 10 has an overall length from the closed end 12 to the open end 14 that will permit the sleeve to extend over the arm of a patient so that the closed end 12 covers the patient's hand and the open end 14 is in proximity to the patient's shoulder. For example, the sleeve 10 may have a length of approximately 90 cm, the open end 14 may have a width of approximately 40 cm, and the closed end 12 may have a width of approximately 20 cm. FIG. 3 is a view looking into the sleeve from the open end 14.

According to embodiments of the disclosure, the sleeve 10 includes a first sleeve fenestration 30 and a second sleeve fenestration 40 in one of the first or second panels 16, 18 at positions between the closed end 12 and the open end 14. According to an embodiment, for convenience of description, it will be assumed that the sleeve fenestrations 30 and 40 or formed in the second panel 18, although in other embodiments, the sleeve fenestrations may be formed in the first panel 16. The first sleeve fenestration 30 is positioned to be located over a wrist area of a patient's arm to provide a radial access to the patient's arm, and the second fenestration 40 is positioned to be located close to an elbow area of a patient's arm to provide a brachial access to the patient's arm. The second sleeve fenestration 40 is formed in a central portion of the second panel 18, and the first sleeve fenestration is formed between the second sleeve fenestration and the closed end 14. The sleeve fenestrations 30 and 40 are approximately rectangular or elliptical in shape, and have sizes that range from about 2 cm×5 cm to about 10 cm×15 cm.

According to embodiments, the first and second sleeve fenestrations 30, 40 are respectively covered by first and second clear plastic films 32, 42. Each film 32, 42 is substantially rectangular in shape and is sufficiently large to cover an edge area of the sleeve fenestration with a width of about 25 cm around each fenestration. Each clear plastic film 32, 42 is removably attached to the second panel 18 in the edge areas by a first adhesive 21. In some embodiments, each clear plastic film 32, 42 may include a tab 33, 43 along one side thereof to facilitate removal of the sheets from the sleeve 10. The first adhesive 21 is selected to provide a secure but removable attachment of the film 32, 42 to the second panel 18. Such adhesives are well known in the art and can be used for securing sterile drapes to patients in other surgical applications.

According to embodiments, the first and second sleeve fenestrations 30, 40 are respectively further covered by first and second foldable flaps 36, 46. The flaps may be formed of the same material as the sleeve. Each flap 36, 46 is substantially rectangular in shape and is sufficiently large to cover the clear plastic films 32, 42, and extend beyond the clear plastic films 32, 42 on at least one side 34, 44 of the clear plastic films 32, 42 where the flaps 36, 46 are securely attached 22 to the second panel 18. The secure attachment may in the form of a second adhesive, or the first and second flaps 36, 46 may be sewn to the second panel 18, although embodiments are not limited thereto. The second adhesive is selected to provide a secure, non-removable attachment of the flaps 36, 46 to the second panel 18. Such adhesives are well known in the art.

According to embodiments, each of the first and second flaps 36, 46 includes, respectively, a removable first liner 37 and a removable second liner 47 on an inside of the flap 36, 46 that faces the clear plastic films 32, 42 and the second panel 18 when the flaps 36, 46 are in a closed position that covers the clear plastic films 32, 42. The removable liner's 37, 47 of each of the first and second flaps 36, 46 are attached to the first and second flaps 36, 46 by a third adhesive 23. Removal of the liners 37, 47 from the respective flaps 36, 46 allows the flaps 36, 46 to be removably attached to the second panel 18 by the third adhesive 23. The third adhesive 23 is selected to provide a secure but removable attachment of the liners 37, 47 to the flaps 36, 46, and to provide a secure but removable attachment of the flaps 36, 46 to the second panel 18. Such adhesives are well known in the art and are used for securing sterile drapes to patients in other surgical applications.

In addition, according to embodiments, each of the first and second flaps 36, 46 has respective first and second flap fenestrations 38, 48 that penetrate the flap and liner. When each of the first or second flaps 36, 46 is in a closed position that covers the clear plastic films 32 or 42, first and second flap fenestrations 38, 48 respectively correspond to and are aligned with the first and second sleeve fenestrations. The first or second flaps 36, 46 can be secured in the closed position with the first and second flap fenestrations 38, 48 aligned with the first and second sleeve fenestrations 30, 40 by the third adhesive. Each of first and second flap fenestrations 38, 48 is approximately rectangular or elliptical in shape and has a size that is not larger than its respective corresponding first or second sleeve fenestration 30, 40.

According to embodiments, a fourth adhesive 24 is provided on the inner surface of the sleeve 10 in proximity to the open end 14 thereof. The fourth adhesive 24 is covered by a release layer or liner 26 that can be removed to expose the fourth adhesive 24. The fourth adhesive 24 is used to secure areas of the sleeve 10 adjacent the open end 14 to areas of the patient near the shoulder. The fourth adhesive 24 is selected to provide a secure attachment but easy separation from the patient. Such adhesives are well known in the art and are used for securing sterile drapes to patients in other surgical applications. The first, second and fourth adhesives may be formed form the same material.

Figure 4:
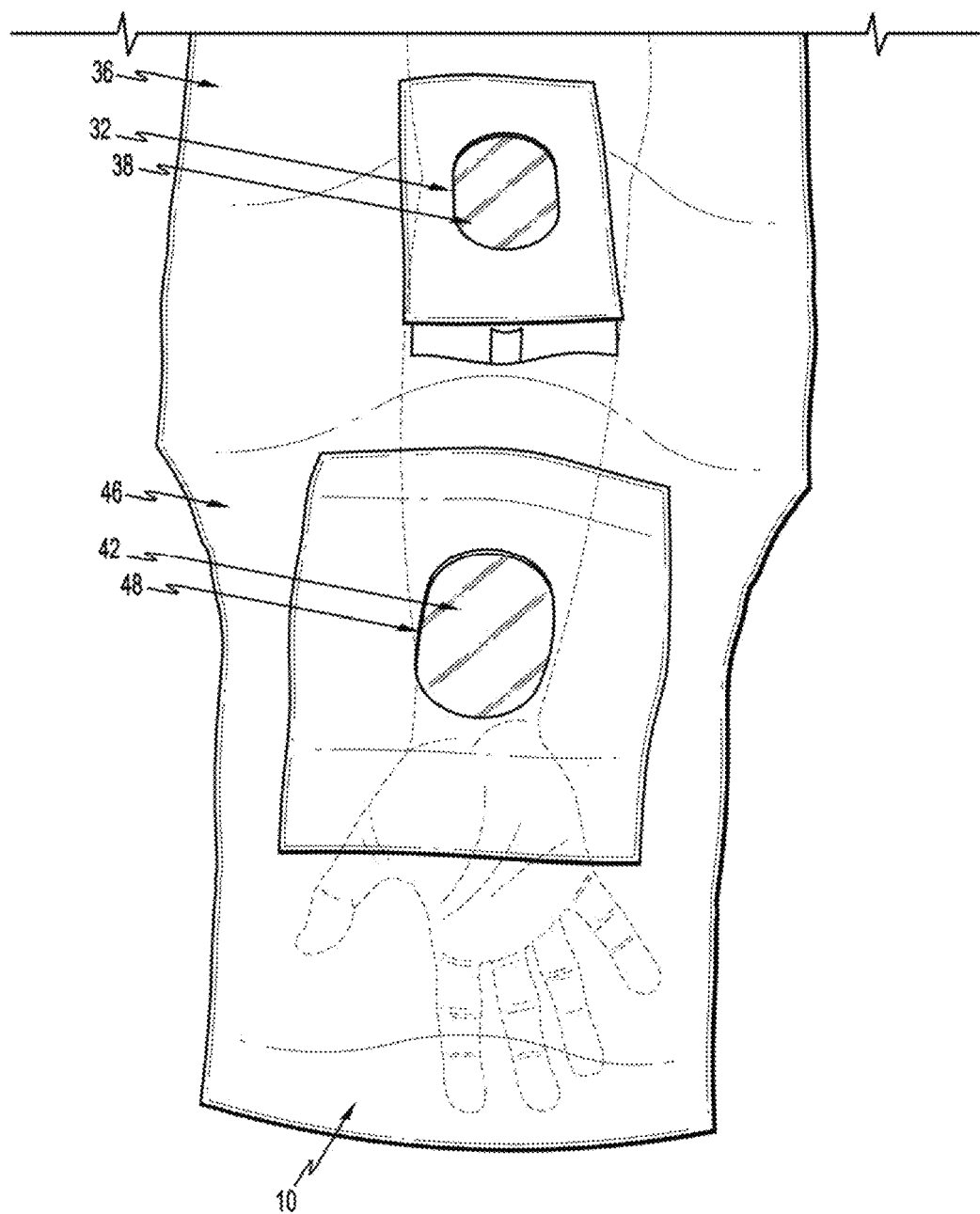
FIG. 4 illustrates a sleeve in place on a patient's arm with both the first and second foldable flaps in a closed position, according to an embodiment of the disclosure.
Figure 5:
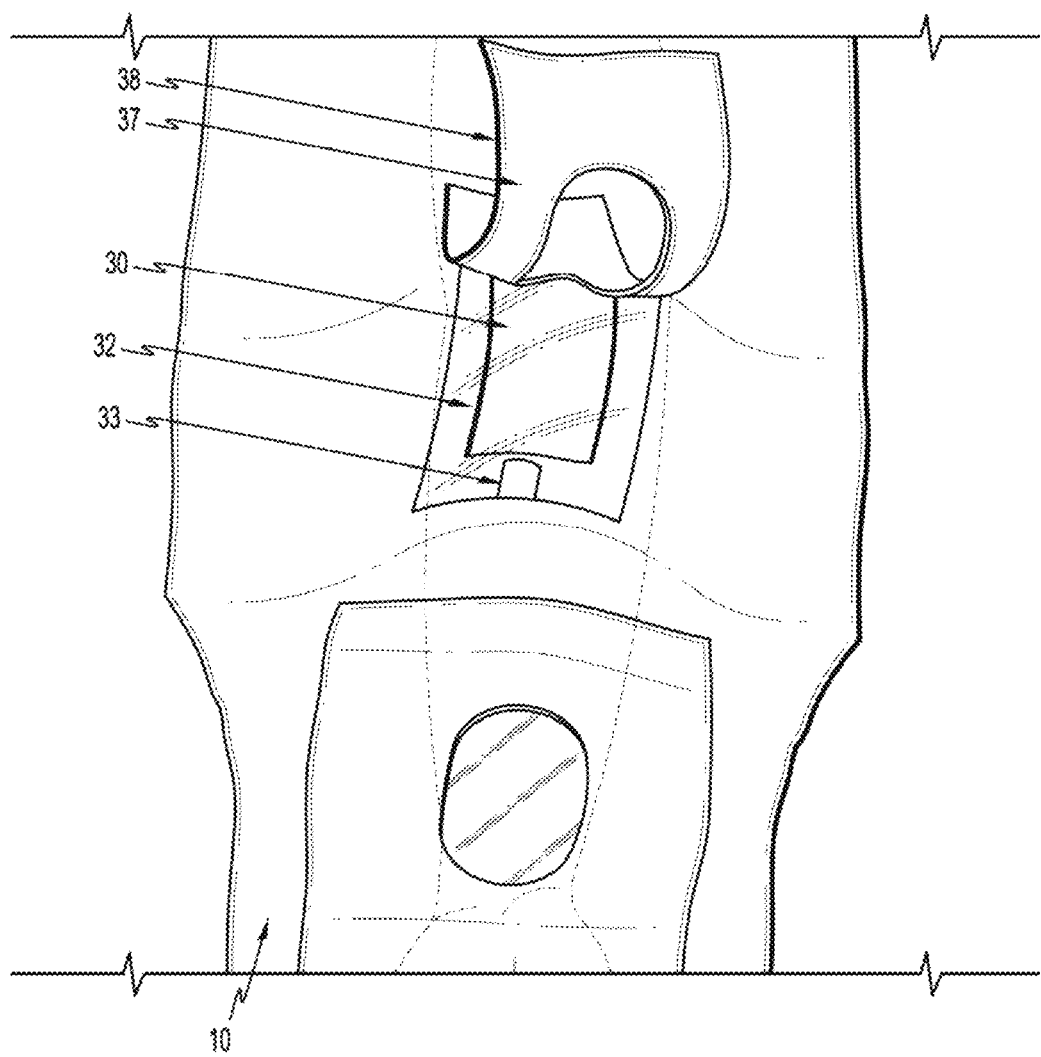
FIG. 5 illustrates a sleeve in place on a patient's arm with the first flap folded back into a partially open position, according to an embodiment of the disclosure.
Figure 6:
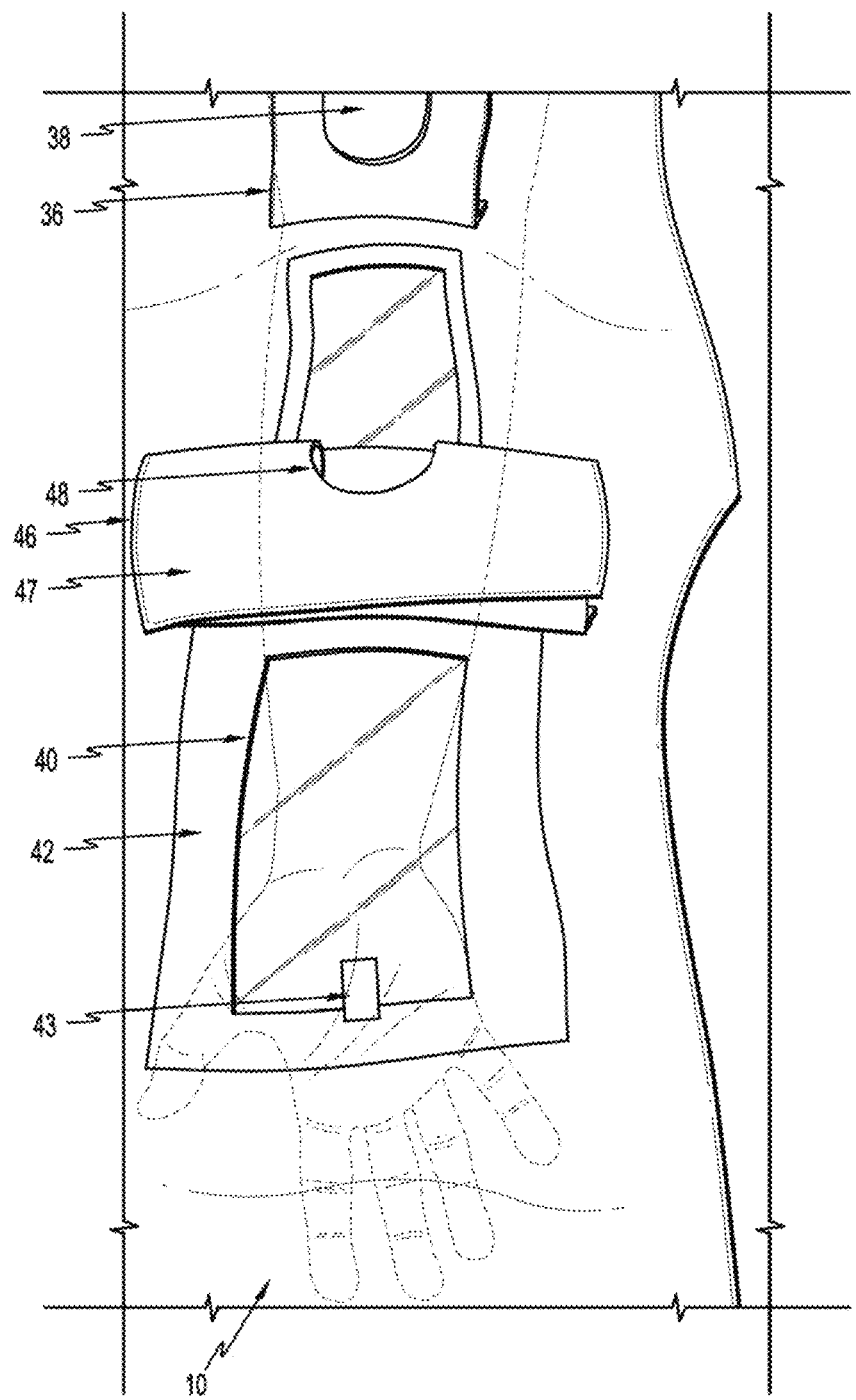
FIG. 6 illustrates a sleeve in place on a patient's arm with the first flap folded back into a completely open position and the second flap folded back into a partially open position, according to an embodiment of the disclosure.

FIG. 4 illustrates a sleeve 10 in place on a patient's arm with both the first and second foldable flaps 36, 46 in a closed position. The first and second clear plastic films 32, 42 are visible through the first and second flap fenestrations 38, 48. FIG. 5 illustrates a sleeve 10 in place on a patient's arm with the first flap 38 folded back into a partially open position. The removable first liner 37 is visible on the underside of the first foldable flap 36, tab 33 is visible on the first clear plastic film 32, and the first sleeve fenestration 30 is visible through the first clear plastic film 32. FIG. 6 illustrates a sleeve 10 in place on a patient's arm with the first flap 36 folded back into a completely open position and the second flap 46 folded back into a partially open position. The second flap 46 is also folded forward to avoid blocking the first fenestration 30. The removable second liner 47 is visible on the underside of the second foldable flap 46, tab 43 is visible on the second clear plastic film 42, and the second sleeve fenestration 40 is visible through the second clear plastic film 42.

The sleeve 10 is employed by pulling the sleeve over the arm of the patient on an operating table until the sleeve can be secured to the patient's shoulder. The liner 26 is then removed from the fourth adhesive 24 so that the sleeve can be secured to the patient's shoulder. One of the first and second sleeve fenestrations 30, 40 can be selected for use. For convenience of description, the use of the sleeve will be described with reference to the first sleeve fenestration 30, but it is to be understood that the following description can also refer to the second sleeve fenestration 40. The first flap 36 that covers the first sleeve fenestration 30 can be folded back to an open position that exposes the first clear plastic film 32. The first clear plastic film 32 can be separated from the second panel 18 by pulling upward on the tab 33 to expose the patient's arm through the first sleeve fenestration. At this time, the section of the patient's arm exposed through the first sleeve fenestration 30 can be sterilized. The first liner 37 is then removed from the first flap 36, after which the first flap 36 is returned to the closed position. A portion of the patient's arm will still be exposed through the first flap fenestration 38 of the first flap 36. A catheter can then be inserted into a blood vessel through the portion of the patient's arm exposed through the first flap fenestration 38. After completion of the procedure, the sleeve 10 can be disposed.

According to an embodiment, the sleeve 10 can be packaged in a sterile enclosure, such as a poly-paper laminated enclosure, and will be opened and accessed immediately prior to a procedure in the operating room or other medical facility. When removed from the sterile enclosure, the sleeve is folded and has a paper covering. The sleeve is removed from the covering and put on a patient.

A radial access catheterization sleeve 10 according to an embodiment as described above can be mounted quickly and easily onto a patient by one health care professional. The arm of the patient is substantially completely enclosed to ensure sterility during the procedure. The adhesive around the open end 14 of the sleeve 10 facilitates secure releasable attachment to the shoulder area of the patient. Additionally, the size and shape of the sleeve 10 prevents parts of the sleeve 10 from hanging off the operating table extension in a way that could interfere with the doctor or other health care personnel working near the patient.

The above-described embodiments are one examples of the disposable radial or brachial access catheterization sleeve in accordance with the invention. Fenestrations of different sizes or shapes can be provided in addition to those illustrated herein. Other means for closing the fenestrations also can be provided. The proximal edge of the sleeve is configured as being aligned substantially perpendicular to a longitudinal direction of the sleeve. However, the proximal end can be aligned at an acute angle to the longitudinal direction to nest more securely at the shoulder of the patient. Although only one sleeve is illustrated, sleeves may come in a plurality of different sizes, to accommodate different aged patients. Furthermore, the sleeve can be packaged with and used with a small sterile sheet that can be used to reduce the size of the fenestration in the sleeve.

While embodiments of the present disclosure has been described in detail with reference to exemplary embodiments, those skilled in the art will appreciate that various modifications and substitutions can be made thereto without departing from the spirit and scope of the disclosure as set forth in the appended claims.

The invention claimed is:

1. A catheterization sleeve, comprising:
a first panel and a second panel attached to each other along sides thereof and at one end, wherein a closed distal end and an open proximal end are formed, wherein the sleeve is dimensioned to cover a hand and at least a portion of an arm of a human patient;
a first sleeve fenestration formed through the first panel at a location in a center portion of the first panel between the proximal and distal ends;
a second sleeve fenestration formed through the first panel at a location between the first sleeve fenestration and the closed distal end;
a first clear film that covers the first sleeve fenestration and is attached to the first panel at an edge region of the first panel adjacent to the first sleeve fenestration;

a second clear film that covers the second sleeve fenestration and is attached to the first panel at an edge region of the first panel adjacent to the second sleeve fenestration;

a first foldable flap forming a topmost layer that covers the first clear film and the first sleeve fenestration, wherein the first foldable flap includes a first liner removably attached to an inner surface of the first foldable flap that faces the first clear film and the first sleeve fenestration when the first foldable flap is in a closed position, and a first flap fenestration the penetrates the first foldable flap and the first liner;

a second foldable flap forming a topmost layer that covers the second clear film and the second sleeve fenestration, wherein the second foldable flap includes a second liner removably attached to an inner surface of the second foldable flap that faces the second clear film and the second sleeve fenestration when the second foldable flap is in a closed position and a second flap fenestration that penetrates the second foldable flap and the second liner, wherein the first flap fenestration of the first foldable flap is aligned with the first sleeve fenestration when the first foldable flap is in the closed position, and a size of the first flap fenestration is less than or equal to a size of the first sleeve fenestration, and wherein the second flap fenestration of the second foldable flap is aligned with the second sleeve fenestration when the second foldable flap is in the closed position, and a size of the second flap fenestration is less than or equal to a size of the second sleeve fenestration, and wherein the first and second clear films are sandwiched directly between the first panel and the first and second liners, respectively, and are configured to be removed during use.

2. The catheterization sleeve of claim 1, further comprising an adhesive substantially adjacent to the open proximal end for securing the proximal end of the sleeve to the patient at a location in proximity to a shoulder of the patient, and a removable cover that covers the adhesive.

3. The catheterization sleeve of claim 1, wherein the first clear film and the second clear film are each removably attached to the first panel by an adhesive, and wherein each of the first and second clear films includes a pull tab attached thereto, wherein each of the first or second clear films is removable from the first panel by application of a pulling force to the respective pull tab.

4. The catheterization sleeve of claim 1, wherein the first foldable flap is securely attached to the first panel wherein the first foldable flap can be folded back to expose the first clear film; and wherein the second foldable flap is securely attached to the first panel wherein the second foldable flap can be folded back to expose the second clear film.

\* \* \* \* \*